United States Patent [19]

Solomon

[11] Patent Number: 5,222,504
[45] Date of Patent: Jun. 29, 1993

[54] DISPOSABLE NEUROLOGICAL PINWHEEL

[76] Inventor: Charles L. Solomon, 12106 Cherry Grove, Moorpark, Calif. 93021

[21] Appl. No.: 833,938

[22] Filed: Feb. 11, 1992

[51] Int. Cl.$^5$ ............................................. A61B 19/00
[52] U.S. Cl. .................................................. 128/744
[58] Field of Search ...................... 128/744, 756, 759; 446/217, 218

[56] References Cited

U.S. PATENT DOCUMENTS

| | | | |
|---|---|---|---|
| 3,074,395 | 1/1963 | Kevorkian | 128/744 |
| 3,512,518 | 5/1970 | Mishkin et al. | 128/756 |
| 3,515,125 | 6/1970 | Ruskin | 128/744 |
| 4,823,806 | 4/1989 | Bajada | 128/744 |
| 4,865,045 | 9/1989 | Monreal | 128/740 |
| 5,022,408 | 6/1991 | Mohajer | 128/759 |

FOREIGN PATENT DOCUMENTS 1066536  1/1984  U.S.S.R. ............................ 128/744

Primary Examiner—Max Hindenburg
Attorney, Agent, or Firm—Louis J. Bachand

[57] ABSTRACT

A disposable neurological tester comprising a many-pointed pinwheel having a hub and an annular radially projecting array of synthetic organic plastic tines for neurological testing stimulation of the skin and flexible against skin penetration, and an elongated synthetic organic plastic handle having a first terminus. The pin wheel is carried at the handle first terminus on an axle supported from a single side with the tines projecting for skin stimulation, whereby precise locus of skin stimulation by said wheel is viewable by the tester operator from the side of the pin wheel which is free of handle support.

12 Claims, 1 Drawing Sheet

U.S. Patent
June 29, 1993
5,222,504
FIG. 1
FIG. 2
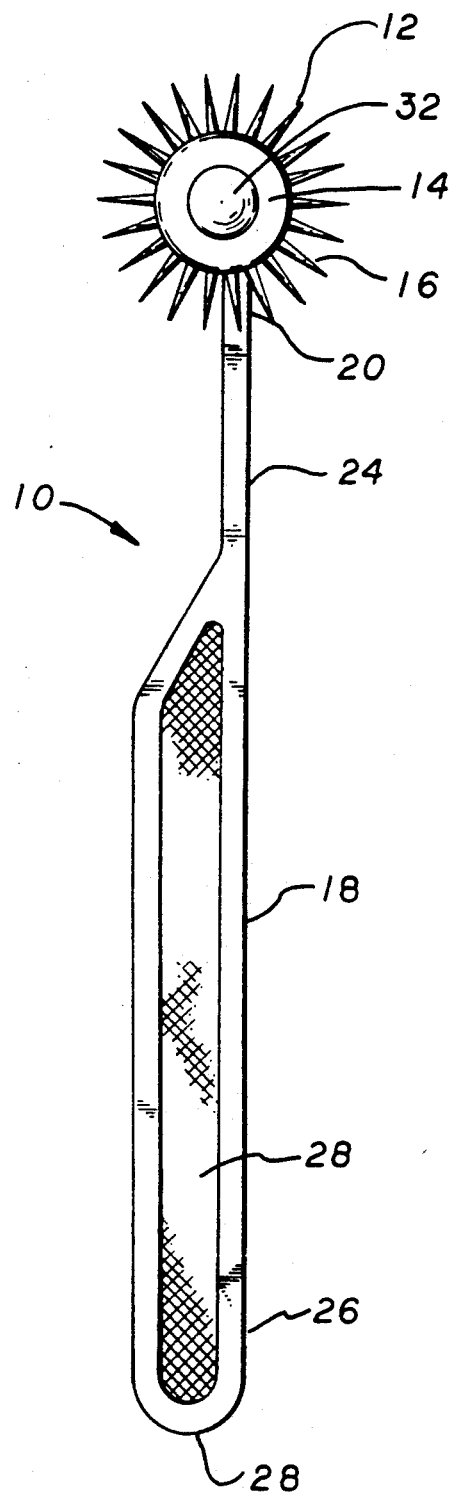
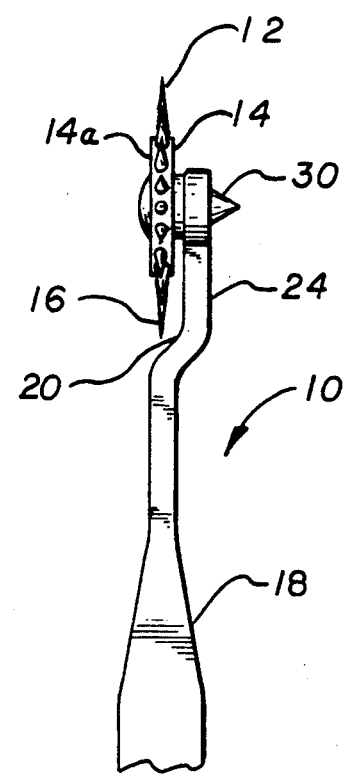
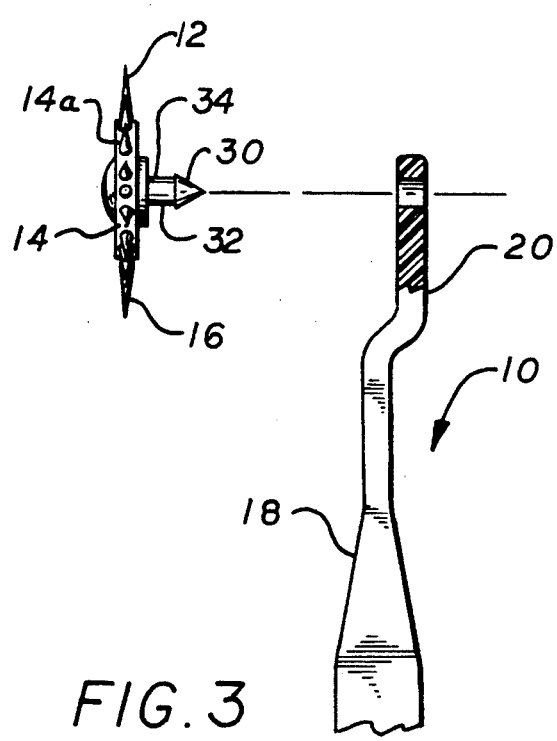
FIG. 3

DISPOSABLE NEUROLOGICAL PINWHEEL

TECHNICAL FIELD

This invention has to do with neurological testing, and more particularly with improved neurological testing devices which are disposable to avoid dangers of contamination, and supported from a single side, cantilever fashion, to enable closer observation of traverse over the appropriate area of skin innervated by a particular nerve, or dermatome. The improved devices comprise a pinwheel having a plurality of radially projecting points normally incapable of penetrating the skin, a supporting handle defining relatively enlarged sharp and dull points for added testing convenience, and which is fabricated of disposable plastic material for increased safety against cross-contamination between patients and/or doctors.

BACKGROUND

Neurological testing is carried out by medical professionals to evaluate the nerve response of patients as an indicator of health conditions. In one such evaluation, the patient's skin is run across with a pinwheel having a plurality of outstanding pins, or radial projections, sharp-ended, to determine the extent of feeling in the underlying dermatome or area of interest. In addition to the pinwheel evaluation, the medical professional will use both relatively dull and relatively pointed instruments to detect discriminatory capabilities of sharp to dull.

Neurological pinwheels have long been available as metal, sterilizable instruments comprising a handle having a forked end, and a pinwheel mounted on an axle carried between the legs of the fork. While the neurological pinwheel is designed and used as a non-invasive instrument, it is possible for penetration of the skin to occur owing to the sharpness and strength of the metal projections, i.e. if the patient unexpectedly moves the extremity being tested into the instrument before the medical professional can remove the pinwheel from the skin. Visual reference to the skin area being tested is partially blocked by the known instruments in that the pinwheel is between the legs of the supporting fork of the handle and the contact points of the pinwheel projections are not conveniently visible.

The potential spread of viral infections including hepatitis B and HIV in the clinical setting makes the reuse of instruments problematic, but sterilizable metal instruments are too costly to not reuse many times.

SUMMARY OF THE INVENTION

It is an object, therefore, of the present invention to provide improvements in neurological testing devices. It is another object to provide a new neurological testing device of the pinwheel type, and one which avoids the problems with known pinwheel testing devices. It is yet another object to provide a pinwheel testing device which is disposable after a single use, normally non-penetrative of the skin even when the patient unexpectedly moves, and which provides a ready view of the area being tested and is low cost and effective for its purpose.

These and other objects of the invention to appear hereinafter are realized in a neurological tester comprising a many-pointed pinwheel having a hub and an annular radially projecting array of synthetic organic plastic tines, the tines being sized and arranged for neurological testing stimulation of the skin and flexible against skin penetration, and an elongated synthetic organic plastic handle having a first terminus, the pinwheel being carried at the handle first terminus on an axle supported from a single side with the tines projecting for skin stimulation, the handle having a second terminus, a gripping surface formed on the handle more closely adjacent the handle second terminus than the handle first terminus, whereby precise locus of skin stimulation by said wheel is viewable by the tester operator by exposure to view of the side of the pinwheel which is outboard of the supporting handle.

In particular embodiments, typically the pinwheel hub and tines are integrally molded, the pinwheel tines extend from one-third to one and one-third the radius of the pinwheel hub, the wheel tines project radially of the pinwheel hub, and the handle first terminus defines a dull edged surface for neurological testing.

In a particularly preferred embodiment, typically there is further provided a pin supported by the handle first terminus, the pin defining an axle for the pinwheel, the pin is sharply pointed at one end for use in neurological testing, and the pinwheel is rotatably supported on the pin freely of support on one side of the pinwheel to permit easy observation of the area below the pinwheel from the free side of the pinwheel.

In this and like embodiments typically, the pinwheel hub and tines are integrally molded, the wheel tines extend from one-third to one and one-third the radius of the pinwheel hub, the pinwheel tines project radially of the pinwheel hub, and the handle first terminus defines a dull edged surface in contrast to the sharply pointed pin and both for neurological testing.

THE DRAWINGS

The invention will be further described in conjunction with the attached drawings in which:

FIG. 1 is a side elevation view of the invention disposable pinwheel neurological tester;

FIG. 2 is a fragmentary plan view thereof; and,

FIG. 3 is a view like FIG. 2 of the tester partially disassembled.

DETAILED DESCRIPTION

With reference to the drawings in detail, in FIGS. 1-3, the disposable neurological tester according to the invention is shown at 10 and comprises a many-pointed pinwheel 12 having a hub 14 and an annular radially projecting array of synthetic organic plastic tines 16. The tines 16 are sized and arranged as shown to be suited for neurological testing stimulation of the skin. They are generally stiff so as to provide adequate stimulation to the skin, but also sufficiently flexible when forced back against the hub 14, such as by a sudden upward movement of the patient, to avoid skin penetration. This feature is a further safeguard against unwanted invasive procedures and a protection against contamination by patient's blood. The tester 10 further comprises an elongated synthetic organic plastic handle 18 having a first terminus 20. The pin wheel 12 is carried at said handle first terminus 20 on an axle 32 supported from a single side 24 of the handle 18 with its tines projecting for skin stimulation as shown. It will be observed that it is possible to view the area under the pinwheel 12 more easily from the side of the pinwheel that is outboard of the supporting handle portion 24. Previous pinwheel neurological testers have been made of metal and have had forked ends with the pinwheel supported between them. In such testers the area of contact of the pinwheel tines is not readily observable, but in the present device, omission of the handle fork on one side of the pinwheel makes observation of the dermatome to which the pinwheel is applied readily achievable by exposure to view of the side of the pinwheel which is free of handle 18 support (left side of the pinwheel 12 in the drawings).

The tester handle 18 has a second terminus 26 and a gripping surface 28 formed closely adjacent thereto.

The handle 18 and pinwheel 12 are suitably formed of synthetic organic plastic which is resistant to chemicals and heat that may be encountered in the clinical setting. Suitable plastics include nylons, olefins, styrene copolymers, acrylic polymers and copolymers, polyaldehydes, polysulfones and polycarbonates, all in molecular weights and modulus appropriate to the indicated function. The handle and pinwheels are typically fabricated of materials suited particularly to the different purposes of these components of the tester 10. The pinwheel hub 14 and tines 16 are suitably integrally molded.

While size of tines is not narrowly critical, in most cases the pinwheel tines will extend from one-third to one and one-third times the radius of the pinwheel hub 14. The orientation of the tines 16 is not narrowly critical but typically will be such that the pinwheel tines project radially of the wheel hub 14 periphery 14a.

It is sometimes a convenience to the medical professional to have the ability to readily test the patient with grossly rounded or acute surfaces in addition to the pinwheel. For facilitating this, the present tester 10 in its preferred modes has the handle second terminus 26 define a rounded i.e. dull edged surface 28 for neurological testing.

For an acute surface, the present tester 10 provides a sharply pointed end 30 to the axle 32 (defined by pin 34) which supports the pinwheel 12 in handle terminus 24 at its hub 14, as shown.

It will be observed from the drawings that the pinwheel 12 is rotatably supported on the pin 34 freely of support on one side of the pinwheel to permit easy observation of the area below said pinwheel from the free side, or outboard side, of the pinwheel.

The foregoing objects are thus achieved, the device is fabricated of plastic rather than costly metal and is thus disposable as well as more efficient and safe.

I claim:

1. Disposable neurological tester comprising a many-pointed pinwheel having a hub and an annular radially projecting array of synthetic organic plastic tines, said tines being sized and arranged for neurological testing stimulation of the skin and flexible against skin penetration, and an elongated synthetic organic plastic handle having a first terminus, said pinwheel being carried at said handle first terminus on an axle supported from a single side with said tines projecting for skin stimulation, said handle having a second terminus, a gripping surface formed on said handle more closely adjacent said handle second terminus than said handle first terminus, whereby precise locus of skin stimulation by said pinwheel is viewable by the tester operator by exposure to view of the side of said pinwheel which is outboard of said supporting handle.

2. Disposable neurological tester according to claim 1, in which said pinwheel hub and tines are integrally molded.

3. Disposable neurological tester according to claim 1, in which said wheel tines extend from one-third to one and one-third the radius of said pinwheel hub.

4. Disposable neurological tester according to claim 1, in which said pinwheel tines project normal to the said wheel hub.

5. Disposable neurological tester according to claim 1, in which said handle first terminus defines a dull edged surface for neurological testing.

6. Disposable neurological tester according to claim 1, including also a pin supported by said handle first terminus, said pin defining an axle for said pinwheel.

7. Disposable neurological tester according to claim 6, in which said pin is sharply pointed at one end for neurological testing.

8. Disposable neurological tester according to claim 7, in which said pinwheel is rotatably supported on said pin freely of support on one side of said pinwheel to permit easy observation of the area below said pinwheel from the free side of said pinwheel.

9. Disposable neurological tester according to claim 8, in which said pinwheel hub and tines are integrally molded.

10. Disposable neurological tester according to claim 9, in which said pinwheel tines extend from one-third to one and one-third the radius of said wheel hub.

11. Disposable neurological tester according to claim 10, in which said pinwheel tines project radially of the periphery of said wheel hub.

12. Disposable neurological tester according to claim 11, in which said handle first terminus defines a dull edged surface in contrast to said sharply pointed pin and both for neurological testing.

* * * * *